United States Patent
Zhao et al.

(10) Patent No.: US 10,393,647 B1
(45) Date of Patent: Aug. 27, 2019

(54) SYSTEM, METHOD, AND COMPUTER PROGRAM PRODUCT FOR AUTOMATICALLY DETERMINING A PARAMETER CAUSING AN ABNORMAL SEMICONDUCTOR METROLOGY MEASUREMENT

(71) Applicant: KLA-Tencor Corporation, Milpitas, CA (US)

(72) Inventors: Qiang Jimmy Zhao, Milpitas, CA (US); Liequan Lee, Fremont, CA (US); Jonathan Ian Iloreta, Menlo Park, CA (US); Hong Qiu, Union City, CA (US); Leonid Poslavsky, Belmont, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 796 days.

(21) Appl. No.: 14/578,245

(22) Filed: Dec. 19, 2014

Related U.S. Application Data

(60) Provisional application No. 61/918,105, filed on Dec. 19, 2013.

(51) Int. Cl.
*G01N 21/25* (2006.01)

(52) U.S. Cl.
CPC ....... *G01N 21/255* (2013.01); *G01N 2201/12* (2013.01)

(58) Field of Classification Search
None
See application file for complete search history.

(56) References Cited

U.S. PATENT DOCUMENTS

| 5,608,526 A | 3/1997 | Piwonka-Corle et al. |
| 5,859,424 A | 1/1999 | Norton et al. |
| 6,429,943 B1 | 8/2002 | Opsal et al. |

(Continued)

OTHER PUBLICATIONS

U.S. Appl. No. 61/830,536, filed Jun. 3, 2013.

(Continued)

*Primary Examiner* — Manuel L Barbee
(74) *Attorney, Agent, or Firm* — Zilka-Kotab, P.C.

(57) ABSTRACT

A system, method, and computer program product are provided for automatically determining a parameter causing an abnormal semiconductor metrology measurement. In use, an abnormal semiconductor metrology measurement measured from a fabricated semiconductor component is received. At least one parameter of the fabricated semiconductor component causing the abnormal semiconductor metrology measurement is then automatically determined by one or more hardware processors. In particular, the one or more hardware processors determine a subset of parameters of the fabricated semiconductor component as potential sources of the abnormal semiconductor metrology measurement, rank the parameters in the determined subset of parameters, select an Nth number of the parameters in the determined subset of parameters in accordance with the ranking, and then analyze each of the selected parameters to identify one or more of the selected parameters as the at least one parameter of the fabricated semiconductor component causing the abnormal semiconductor metrology measurement.

17 Claims, 12 Drawing Sheets

(56) References Cited

U.S. PATENT DOCUMENTS

| | | | |
|---|---|---|---|
| 7,174,281 B2 * | 2/2007 | Abercrombie | G06Q 10/043 700/108 |
| 7,363,098 B2 * | 4/2008 | Ng | G05B 19/41875 700/108 |
| 7,478,019 B2 | 1/2009 | Zangooie et al. | |
| 7,933,026 B2 | 4/2011 | Opsal et al. | |
| 9,291,554 B2 | 3/2016 | Kuznetsov et al. | |
| 9,739,702 B2 | 8/2017 | Bringoltz et al. | |
| 9,915,522 B1 | 3/2018 | Jiang et al. | |
| 2003/0208286 A1 * | 11/2003 | Abercrombie | G06Q 10/043 700/31 |
| 2007/0142951 A1 * | 6/2007 | Ng | G05B 19/41875 700/110 |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |

OTHER PUBLICATIONS

U.S. Appl. No. 61/761,146, filed Feb. 5, 2013.
U.S. Appl. No. 61/738,760, filed Dec. 18, 2012.
U.S. Appl. No. 61/745,981, filed Dec. 26, 2012.

* cited by examiner

| Select Parameters | | | | |
|---|---|---|---|---|
| Select | Name | Nominal | Float | Layer |
| ■ | OrthogonalityAngle | 90 | | UnitCell |
| ☐ | PeriodX | 400 | | UnitCell |
| ☐ | PeriodY | 200 | | UnitCell |
| ☐ | Notch | 5 | | UnitCell |
| ☐ | L1_HT | 4 | | L1 |
| ☑ | G2_SWA | 90 | | G2 |
| ☐ | G2_HT | 50 | Floated | G2 |
| ☑ | G2_OrientationAngle | 90 | | G2 |
| ☐ | G3_MCD | 205 | Floated | G3 |
| ☐ | G3_SWA | 86 | Floated | G3 |
| ☑ | G3_HT | 290 | Floated | G3 |
| ☑ | G3_OrientationAngle | 90 | | G3 |
| ☑ | G3_TopRounding | 35 | | G3 |

SYSTEM, METHOD, AND COMPUTER PROGRAM PRODUCT FOR AUTOMATICALLY DETERMINING A PARAMETER CAUSING AN ABNORMAL SEMICONDUCTOR METROLOGY MEASUREMENT

RELATED APPLICATION(S)

This application claims the benefit of U.S. Provisional Patent Application No. 61/918,105 filed Dec. 19, 2013, the entire contents of which are incorporated herein by reference.

FIELD OF THE INVENTION

The present invention relates to semiconductor metrology, and more particularly to abnormal measurements occurring in semiconductor metrology.

BACKGROUND

Semiconductor metrology generally involves measuring various physical features of a fabricated semiconductor component. For example, structural and material characteristics (e.g. material composition, dimensional characteristics of structures and films such as film thickness and/or critical dimensions of structures, overlay, etc.) associated with various semiconductor fabrication processes can be measured using semiconductor metrology tools.

Once a measurement is obtained using a semiconductor metrology tool, the measurement may be analyzed to determine whether it is abnormal. An abnormal measurement may be one that is unexpected, such as one that differs from an expected measurement derived from a model of the semiconductor component. In the past, abnormal measurements have either been disregarded or have been manually analyzed to determine their root cause.

Disregarding an abnormality is generally problematic since it may result in the fabrication of semiconductor components that that are deficient in terms of the specification given by the model. However, manually analyzing the abnormal measurement to determine its root cause is difficult and time consuming, since typically a person would be required to test the numerous parameters involved in the semiconductor fabrication process, one or more of which could be causing the abnormality. There is thus a need for addressing these and/or other issues associated with the prior art.

SUMMARY

A system, method, and computer program product are provided for automatically determining a parameter causing an abnormal semiconductor metrology measurement. In use, an abnormal semiconductor metrology measurement measured from a fabricated semiconductor component is received. At least one parameter of the fabricated semiconductor component causing the abnormal semiconductor metrology measurement is then automatically determined by one or more hardware processors. In particular, the one or more hardware processors determine a subset of parameters of the fabricated semiconductor component as potential sources of the abnormal semiconductor metrology measurement, rank the parameters in the determined subset of parameters, select an Nth number of the parameters in the determined subset of parameters in accordance with the ranking, and then analyze each of the selected parameters to identify one or more of the selected parameters as the at least one parameter of the fabricated semiconductor component causing the abnormal semiconductor metrology measurement.

BRIEF DESCRIPTION OF THE DRAWINGS

FIGS. 4A-4E illustrate screenshots of a user interface of a software program executable to determine a parameter causing an abnormal semiconductor metrology measurement, in accordance with an embodiment.

DETAILED DESCRIPTION

In the field of semiconductor metrology, a metrology tool may comprise an illumination system which illuminates a target, a collection system which captures relevant information provided by the illumination system's interaction (or lack thereof) with a target, device or feature, and a processing system which analyzes the information collected using one or more algorithms. Metrology tools can be used to measure structural and material characteristics (e.g, material composition, dimensional characteristics of structures and films such as film thickness and/or critical dimensions of structures, overlay, etc.) associated with various semiconductor fabrication processes. These measurements are used to facilitate process controls and/or yield efficiencies in the manufacture of semiconductor dies.

The metrology tool can comprise one or more hardware configurations which may be used in conjunction with certain embodiments of this invention to, e.g., measure the various aforementioned semiconductor structural and material characteristics. Examples of such hardware configurations include, but are not limited to, the following.

Spectroscopic ellipsometer (SE)
 SE with multiple angles of illumination
 SE measuring Mueller matrix elements (e.g. using rotating compensator(s))
 Single-wavelength ellipsometers
 Beam profile ellipsometer (angle-resolved ellipsometer)
 Beam profile reflectometer (angle-resolved reflectometer)
 Broadband reflective spectrometer (spectroscopic reflectometer)
 Single-wavelength reflectometer
 Angle-resolved reflectometer
 Imaging system
 Scatterometer (e.g. speckle analyzer)

Figure 1:
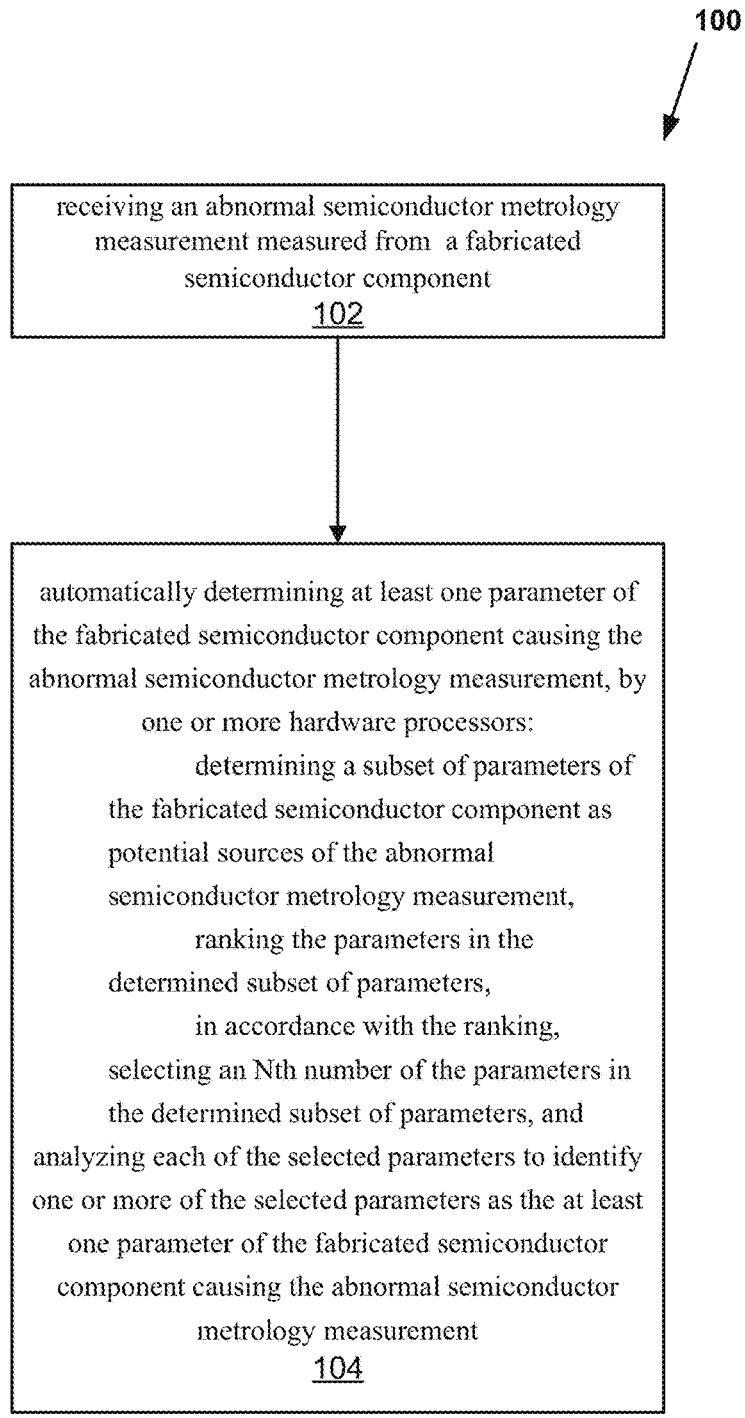
FIG. 1 illustrates a method for determining a parameter causing an abnormal semiconductor metrology measurement, in accordance with an embodiment.

The hardware configurations can be separated into discrete operational systems. On the other hand, one or more hardware configurations can be combined into a single tool. One example of such a combination of multiple hardware configurations into a single tool is shown in FIG. 1 of U.S. Pat. No. 7,933,026 which is hereby incorporated by reference in its entirety for all purposes. FIG. 1 of U.S. Pat. No.

7,933,026 provides an illustration of multiple metrology heads integrated on the same tool. However, in many cases, multiple metrology tools are used for measurements on a single or multiple metrology targets. This is described, for example, in U.S. Pat. No. 7,478,019, "Multiple tool and structure analysis," which is also hereby incorporated by reference in its entirety for all purposes.

The illumination system of the certain hardware configurations includes one or more light sources. The light source may generate light having only one wavelength (i.e., monochromatic light), light having a number of discrete wavelengths (i.e., polychromatic light), light having multiple wavelengths (i.e., broadband light) and/or light the sweeps through wavelengths, either continuously or hopping between wavelengths (i.e. tunable sources or swept source). Examples of suitable light sources are: a white light source, an ultraviolet (UV) laser, an arc lamp or an electrode-less lamp, a laser sustained plasma (LSP) source, for example those commercially available from Energetiq Technology, Inc., Woburn, Mass., a super-continuum source (such as a broadband laser source) such as those commercially available from NKT Photonics Inc., Morganville, N.J., or shorter-wavelength sources such as x-ray sources, extreme UV sources, or some combination thereof. The light source may also be configured to provide light having sufficient brightness, which in some cases may be a brightness greater than about 1 W/(nm cm$^2$ Sr). The metrology system may also include a fast feedback to the light source for stabilizing its power and wavelength. Output of the light source can be delivered via free-space propagation, or in some cases delivered via optical fiber or light guide of any type.

The metrology tool is designed to make many different types of measurements related to semiconductor manufacturing. Certain embodiments may be applicable to such measurements. For example, in certain embodiments the tool may measure characteristics of one or more targets, such as critical dimensions, overlay, sidewall angles, film thicknesses, process-related parameters (e.g., focus and/or dose). The targets can include certain regions of interest that are periodic in nature, such as for example gratings in a memory die. Targets can include multiple layers (or films) whose thicknesses can be measured by the metrology tool. Targets can include target designs placed (or already existing) on the semiconductor wafer for use, e.g., with alignment and/or overlay registration operations. Certain targets can be located at various places on the semiconductor wafer. For example, targets can be located within the scribe lines (e.g., between dies) and/or located in the die itself. In certain embodiments, multiple targets are measured (at the same time or at differing times) by the same or multiple metrology tools as described in U.S. Pat. No. 7,478,019. The data from such measurements may be combined. Data from the metrology tool is used in the semiconductor manufacturing process for example to feed-forward, feed-backward and/or feed-sideways corrections to the process (e.g. lithography, etch) and therefore, might yield a complete process control solution.

As semiconductor device pattern dimensions continue to shrink, smaller metrology targets are often required. Furthermore, the measurement accuracy and matching to actual device characteristics increase the need for device-like targets as well as in-die and even on-device measurements. Various metrology implementations have been proposed to achieve that goal. For example, focused beam ellipsometry based on primarily reflective optics is one of them and described in the patent by Piwonka-Corle et al. (U.S. Pat. No. 5,608,526, "Focused beam spectroscopic ellipsometry method and system"). Apodizers can be used to mitigate the effects of optical diffraction causing the spread of the illumination spot beyond the size defined by geometric optics. The use of apodizers is described in the patent by Norton, U.S. Pat. No. 5,859,424, "Apodizing filter system useful for reducing spot size in optical measurements and other applications". The use of high-numerical-aperture tools with simultaneous multiple angle-of-incidence illumination is another way to achieve small-target capability. This technique is described, e.g. in the patent by Opsal et al, U.S. Pat. No. 6,429,943, "Critical dimension analysis with simultaneous multiple angle of incidence measurements".

Other measurement examples may include measuring the composition of one or more layers of the semiconductor stack, measuring certain defects on (or within) the wafer, and measuring the amount of photolithographic radiation exposed to the wafer. In some cases, metrology tool and algorithm may be configured for measuring non-periodic targets, see e.g. "The Finite Element Method for Full Wave Electromagnetic Simulations in CD Metrology Using Scatterometry" by P. Jiang et al (expired U.S. Patent Application No. 61/830,536) or "Method of electromagnetic modeling of finite structures and finite illumination for metrology and inspection" by A. Kuznetsov et al. (expired U.S. Patent Application No. 61/761,146).

Measurement of parameters of interest usually involves a number of algorithms. For example, optical interaction of the incident beam with the sample is modeled using EM (electro-magnetic) solver and uses such algorithms as RCWA, FEM, method of moments, surface integral method, volume integral method, FDTD, and others. The target of interest is usually modeled (parameterized) using a geometric engine, or in some cases, process modeling engine or a combination of both. The use of process modeling is described in "Method for integrated use of model-based metrology and a process model," by A. Kuznetsov et al. (expired U.S. Patent Application No. 61/738,760). A geometric engine is implemented, for example, in AcuShape software product of KLA-Tencor.

Collected data can be analyzed by a number of data fitting and optimization techniques an technologies including libraries, Fast-reduced-order models; regression; machine-learning algorithms such as neural networks, support-vector machines (SVM); dimensionality-reduction algorithms such as, e.g., PCA (principal component analysis), ICA (independent component analysis), LLE (local-linear embedding); sparse representation such as Fourier or wavelet transform; Kalman filter; algorithms to promote matching from same or different tool types, and others.

Collected data can also be analyzed by algorithms that do not include modeling, optimization and/or fitting e.g. expired U.S. Patent Application No. 61/745,981.

Computational algorithms are usually optimized for metrology applications with one or more approaches being used such as design and implementation of computational hardware, parallelization, distribution of computation, load-balancing, multi-service support, dynamic load optimization, etc. Different implementations of algorithms can be done in firmware, software, FPGA, programmable optics components, etc.

The data analysis and fitting steps usually pursue one or more of the following goals:

Measurement of CD, SWA, shape, stress, composition, films, band-gap, electrical properties, focus/dose, overlay, generating process parameters (e.g., resist state, partial pressure, temperature, focusing model), and/or any combination thereof;

Modeling and/or design of metrology systems;
Modeling, design, and/or optimization of metrology targets.

The following embodiments disclose a system, method, and computer program product for automatically determining a parameter causing an abnormal semiconductor metrology measurement, such as a metrology measurement measured using one of the tools described above.

As shown, FIG. 1 shows a method 100 for automatically determining a parameter causing an abnormal semiconductor metrology measurement, in accordance with an embodiment. In operation 102, an abnormal semiconductor metrology measurement measured from a fabricated semiconductor component is received. The measurement may be taken using one of the tools described above, and may be a measurement of a structural or material characteristic (e.g. material composition, dimensional characteristics of structures and films such as film thickness and/or critical dimensions of structures, overlay, etc.) associated a semiconductor fabrication process.

In one embodiment, the abnormal semiconductor metrology measurement may be received directly from the system or tool that identified the abnormal semiconductor metrology measurement. Thus, for example, the system or tool may identify the measurement as abnormal with regards to a model of the semiconductor component. Of course, other embodiments are contemplated where the abnormal semiconductor metrology measurement is received by other means.

Next, as shown in operation 104, at least one parameter of the fabricated semiconductor component causing the abnormal semiconductor metrology measurement is automatically determined by one or more hardware processors. In particular with regards to operation 104, the one or more hardware processors determine a subset of parameters of the fabricated semiconductor component as potential sources of the abnormal semiconductor metrology measurement, rank the parameters in the determined subset of parameters, select an Nth number of the (e.g. the top N) parameters in the determined subset of parameters in accordance with the ranking, and then analyze each of the selected parameters to identify one or more of the selected parameters as the at least one parameter of the fabricated semiconductor component causing the abnormal semiconductor metrology measurement.

It should be noted that the hardware processor(s) may be components of a computer system, such as the system described below with reference to FIG. 5. In this way, the processor(s) may perform the sub-steps of operation 104 mentioned above in an entirely automated manner.

Initially in operation 104, a subset of parameters of the fabricated semiconductor component is determined as potential sources of the abnormal semiconductor metrology measurement. This subset may include any parameters of the model of the semiconductor component, such as geometric parameters, material parameters, etc. In one embodiment, the subset may be comprised of parameters that have been selected by a user.

The model of the semiconductor component may be stored in memory and may define floating parameters (e.g. having a range of values) and/or fixed parameters (e.g. having a fixed value), such that the subset of parameters may accordingly be comprised of floating parameters and/or fixed parameters, per the model specification for the semiconductor component. In any case, the subset of parameters of the fabricated semiconductor component is a subset of the parameters defined in the model of the semiconductor component.

When a floating parameter is included in the subset, the floating parameter may be a potential source of the abnormal semiconductor metrology measurement by potentially having a value that is outside of the predefined range of values defined for the parameter. When a fixed parameter is included in the subset, the fixed parameter may be a potential source of the abnormal semiconductor metrology measurement by potentially having a value that varies from the predefined value defined for that parameter.

Additionally, in operation 104, the parameters in the determined subset of parameters are ranked. In one embodiment, the ranking may be based on a goodness of fit (GOF) of the parameters in relation to the abnormal measurement. For example, for each fixed parameter in the subset, a value of the parameter may be adjusted to vary from the corresponding fixed value predefined for that parameter, and a GOF for that adjusted parameter in relation to the abnormal measurement may be determined. As another example, for each floating parameter in the subset, a value of the parameter may be adjusted to be outside of the corresponding range of values predefined for that parameter, and a GOF for that adjusted parameter in relation to the abnormal measurement may be determined. The parameters may then be ranked in an order from best GOF to worst GOF.

In a more specific embodiment, ranking the parameters in the determined subset of parameters may include (1) identifying an abnormal spectra associated with the abnormal measurement, (2) identifying, from a plurality of normal spectra predetermined for the model of the semiconductor component, one of the normal spectra that has a closest fit to the abnormal spectra, (3) calculating a first difference between the abnormal spectra and the normal spectra, (4) for each of the parameters in the subset (a) adjusting a value for the parameter to be outside of one or more values predefined for the parameter, (b) determining a spectra resulting from the adjusted value, and (c) calculating a second difference between the resulting spectra and the abnormal spectra, and finally (5) ranking each of the parameters in the determined subset of parameters based on a correlation between the calculated first difference and the calculated second difference for the parameter.

As noted above, the ranking may be in order of GOF (e.g. between the calculated first difference and the calculated second difference). Optionally, the ranking may be in order (top to bottom) from closest correlation between the calculated first difference and the calculated second difference to farthest correlation between the calculated first difference and the calculated second difference.

Further, in operation 104, an Nth number of the (e.g. the top N) parameters in the determined subset of parameters are selected in accordance with the ranking. The number N may be predetermined (e.g. by a user). As a further option, N may be between 0 and a number of parameters in the subset of parameters of the fabricated semiconductor component that are determined as potential sources of the abnormal semiconductor metrology measurement.

Selecting the N parameters in the determined subset of parameters may involve selecting the Nth number of the parameters in the subset that have been ranked highest in terms of best GOF. Thus, the top N ranked parameters may be utilized in the analysis described below.

In operation 104, then selected N parameters are then analyzed to identify one or more of the selected parameters as the at least one parameter of the fabricated semiconductor component causing the abnormal semiconductor metrology measurement. The selected N parameters may be analyzed individually, or in combinations of two or more. In this way, an individual parameter causing the abnormal semiconductor metrology measurement or a combination of parameters parameter causing the abnormal semiconductor metrology measurement may be identified.

In one embodiment, the analysis may involve performing a regression with the abnormal spectra by floating the selected N parameters and fixing the remaining parameters with baseline values (e.g. determined from regressing the normal spectra). The deviation resulting from the regression of the abnormal spectra in regards to each of the floated N parameters may then be determined and the parameter having the smallest deviation (e.g. best GOF) may be identified as the one causing the abnormal semiconductor metrology measurement.

In a more specific example, analyzing each of the N selected parameters to identify one or more of the selected parameters as the one(s) of the fabricated semiconductor component causing the abnormal semiconductor metrology measurement may include: (1) performing a first regression with a normal spectra, (2) recording results of the first regression, including values for parameters of the semiconductor component, as a baseline, (3) for each individual one of the ranked parameters or a combination of two or more of the ranked parameters, performing a second regression with an abnormal spectra associated with the abnormal measurement using an adjusted value of the individual ranked parameter or the combined two or more of the ranked parameters and using values for remaining parameters of the semiconductor component fixed at the baseline, (4) recording results of the second regression, (5) determining a deviation between each of the results of the first regression and the corresponding result of the second regression, and (6) identifying the individual one of the ranked parameters or the combined two or more of the ranked parameters having the least deviation as the at least one parameter of the fabricated semiconductor component causing the abnormal semiconductor metrology measurement.

In another embodiment, regression may not necessarily be utilized in the analysis, but instead a library having predefined value(s) for parameters may be utilized. In any case, the selected N parameters are analyzed in an automated manner to identify which one (or more) of those selected N parameters caused the abnormal semiconductor metrology measurement.

Moreover, while not shown, it should be noted that a result of the analysis may be displayed to a user. The result may include a list of the analyzed parameters based on each parameter's deviation from the corresponding baseline value noted above. As a further option, the displayed analysis result may include, for each of the parameters, the computed deviation from the corresponding baseline value.

More illustrative information will now be set forth regarding various optional architectures and features with which the foregoing framework may or may not be implemented, per the desires of the user. It should be strongly noted that the following information is set forth for illustrative purposes and should not be construed as limiting in any manner. Any of the following features may be optionally incorporated with or without the exclusion of other features described.

Figure 2:
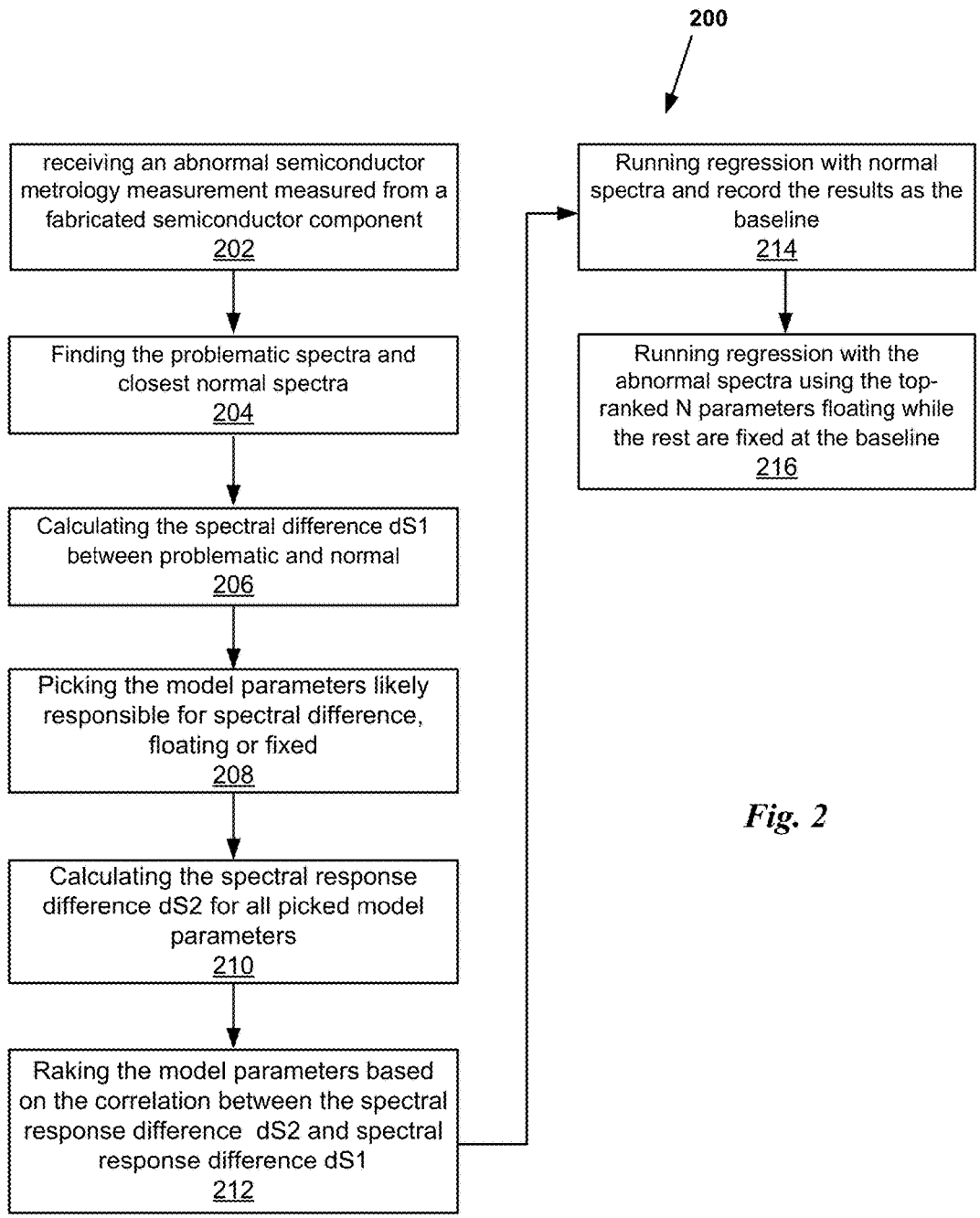
FIG. 2 illustrates a method for determining a parameter causing an abnormal semiconductor metrology measurement using regression, in accordance with an embodiment.

FIG. 2 illustrates a method 200 for determining a parameter causing an abnormal semiconductor metrology measurement using regression, in accordance with an embodiment. As an option, the present method 200 may be carried out in the context of the method 100 of FIG. 1. It should also be noted that the aforementioned definitions may apply during the present description.

As shown in operation 202, an abnormal semiconductor metrology measurement measured from a fabricated semiconductor component is received. The abnormal measurement may involve a floating parameter that is outside of a predefined range or a low normalized GOF (NGOF) between a measured spectra and predefined threshold.

In operation 204, an abnormal spectra associated with the abnormal semiconductor metrology measurement is identified as well as a normal spectra. The normal spectra may be one of a plurality of predefined spectra for a model of the semiconductor component. The normal spectra may be identified as one that has a closest fit with the identified abnormal spectra.

Further, in operation 206, a spectral difference (dS1) between the abnormal spectra and the normal spectra is calculated. A subset of model parameters, floating or fixed, that are likely responsible for the abnormal measurement are then selected, as shown in operation 208. This subset of parameters may be selected by a user familiar with the semiconductor component and/or having a good idea of which floating and/or fixed parameters are likely responsible for the abnormal measurement.

In operation 210, for each of the selected parameters, a spectral response difference (dS2) is calculated. The dS2 for each parameter may be calculated by adjusting a value of the parameter to be outside of a predefined value (or range of values), and then determining a resulting normal spectra and comparing the same to the abnormal spectra. For example, the dS2 for each parameter may be determined by regressing the model with floating that parameter with respect to the other parameters.

The selected parameters are then ranked based on their dS2, as shown in operation 212. Namely, the delta between dS2 and dS1 for each of the selected parameters is determined, and the selected parameters are then ranked (i.e. ordered) based on the deltas. Optionally, the rank may be calculated with correlation to a noise-weighted sensitivity and noise-weighted spectra difference.

As a further option, a min/max envelope for each parameter may be used to compute the correlation between the abnormal spectra and the normal one, and therefore determine the ranks of the parameters. As still yet another option, the selected wavelengths and their ranges can be different in finding out the rank of each parameter.

Moreover, as shown in operation 214, regression with the normal spectra is performed and results are recorded. The results may include baseline values for the parameters. Then, in operation 216, regression with the abnormal spectra is performed with floating the top-ranked N parameters and fixing the remaining parameters at the baseline. As an alternative option, the remaining parameters may not solely be fixed, but a portion thereof may be also be floated along with the top-ranked N parameters. In one embodiment, the user may add additional parameters to be floated or prevent some top-ranked parameters from being floated, as desired. Alternatively, the user may use the derivative information to construct a linear system to compute the possible combination of parameters that could cause excursion after computing the spectra delta to the normal as described above.

After operation 216, the parameters can then be listed in the order of their deviation from the normal values, and the deviations can also be reported (not shown). Note that the above-proposed method 200 may not require regression with all the parameters in the model since only the N ranked parameters are selected. Otherwise, by regressing with all the parameters in the model, the calculation may be unstable due to parameter correlation.

FIGS. 3A-3D illustrate an example of determining a parameter causing an abnormal semiconductor metrology measurement, in accordance with an embodiment. As an option, the present example may be implemented in the context of the method 100 of FIG. 1. It should also be noted that the aforementioned definitions may apply during the present description.

Figure 3A:
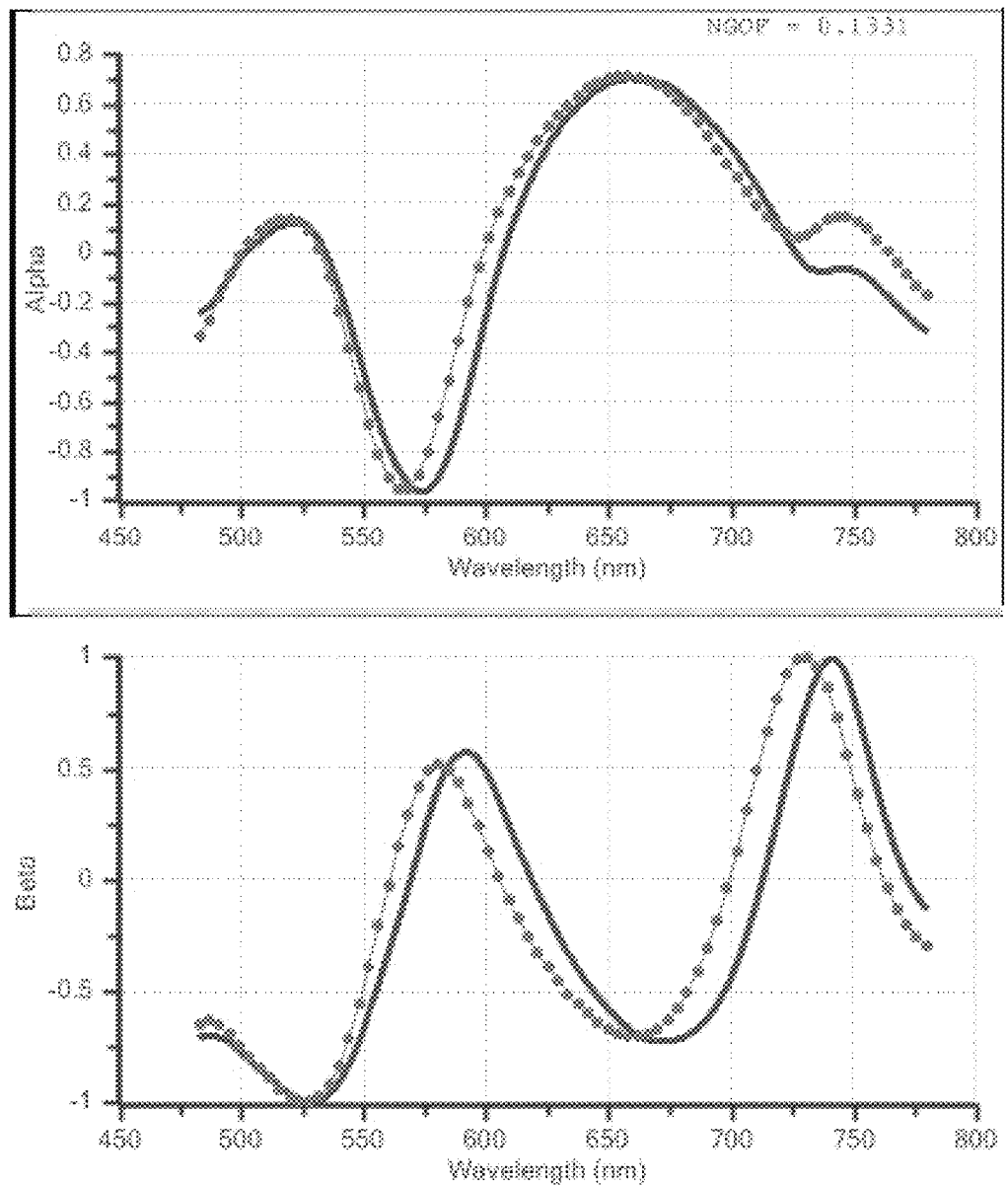
FIGS. 3A-3D illustrate an example of determining a parameter causing an abnormal semiconductor metrology measurement, in accordance with an embodiment.
Figure 3B:
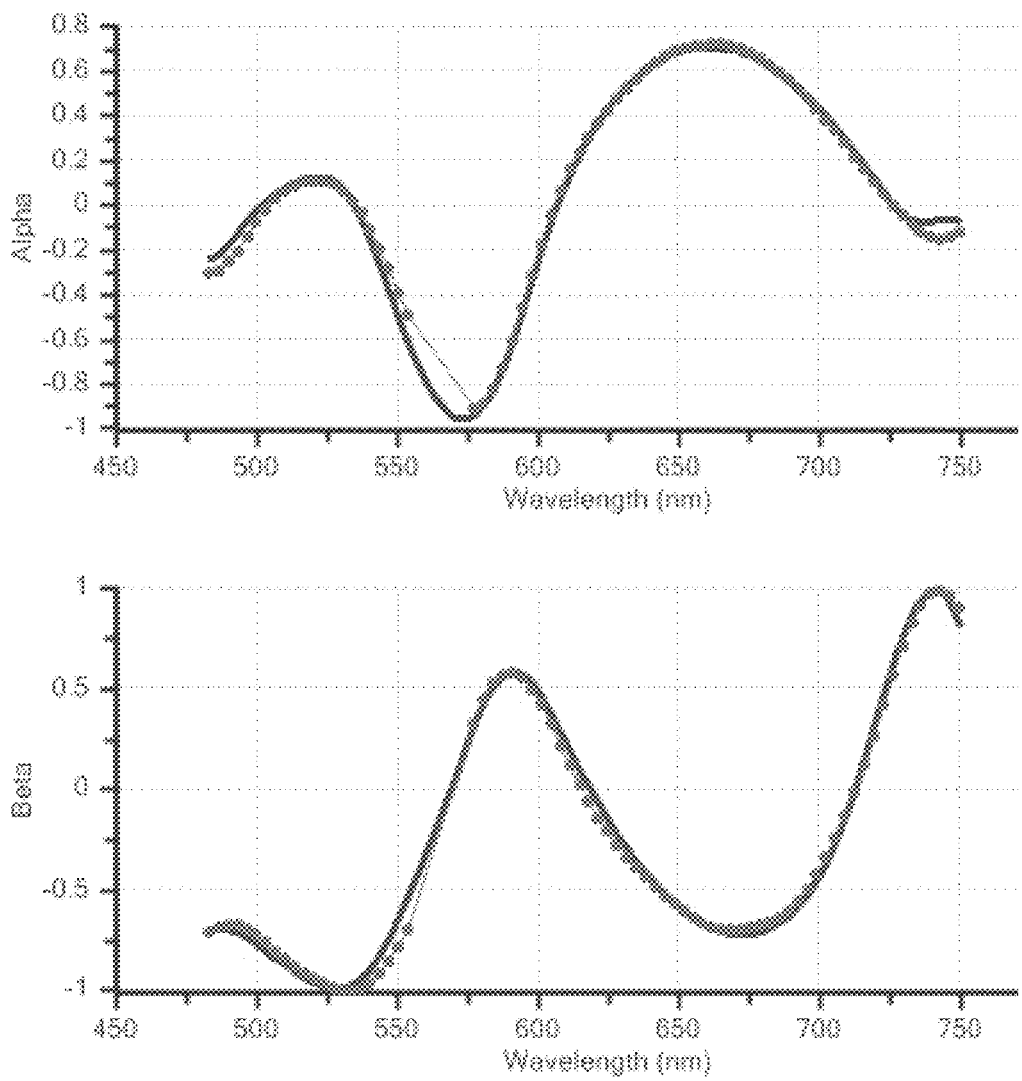

FIG. 3A gives an example of two spectra, where the solid line represents the normal spectra and the dotted line represents the abnormal spectra. As shown in FIG. 3B, the normal and measured spectra are not well-fitted, especially at the region near 750 nm. This low GOF indicates an abnormal semiconductor metrology measurement.

Figure 3C:
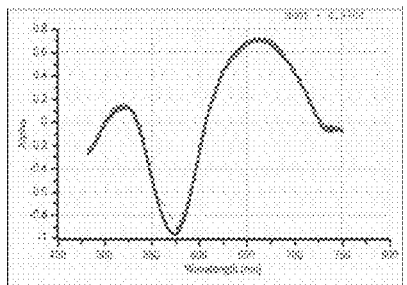
Figure 3C:
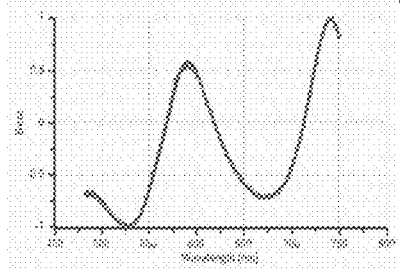
Figure 3C:
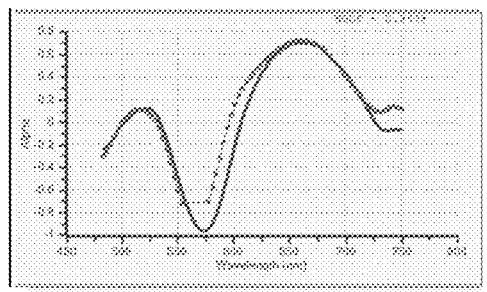
Figure 3C:
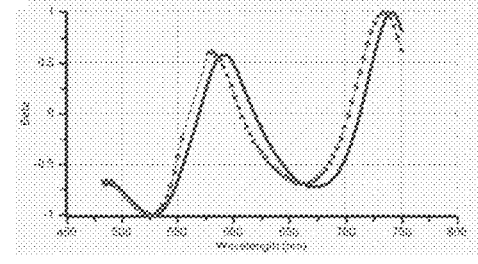
Figure 3C:
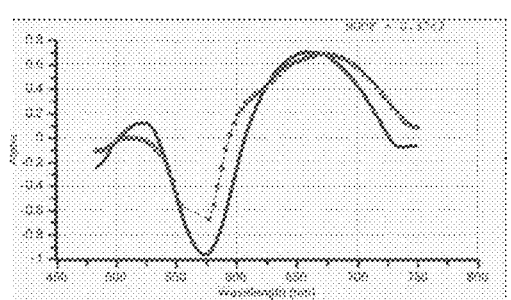
Figure 3C:
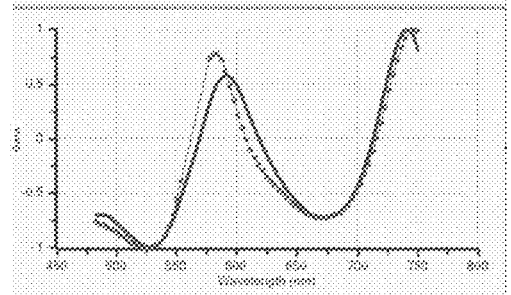

In response to the identified abnormal semiconductor metrology measurement, each parameter in the model (or in a subset thereof) is floated one by one while the rest of the parameters are fixed at the values measured from the normal spectra. Note that the parameters to be tested include both pre-defined fixed parameters and floating ones. Subsequently, a rank based on the GOFs of those runs is determined. FIG. 3C shows the fits of three different parameters, P1, P2, and P3.

Figure 3D:
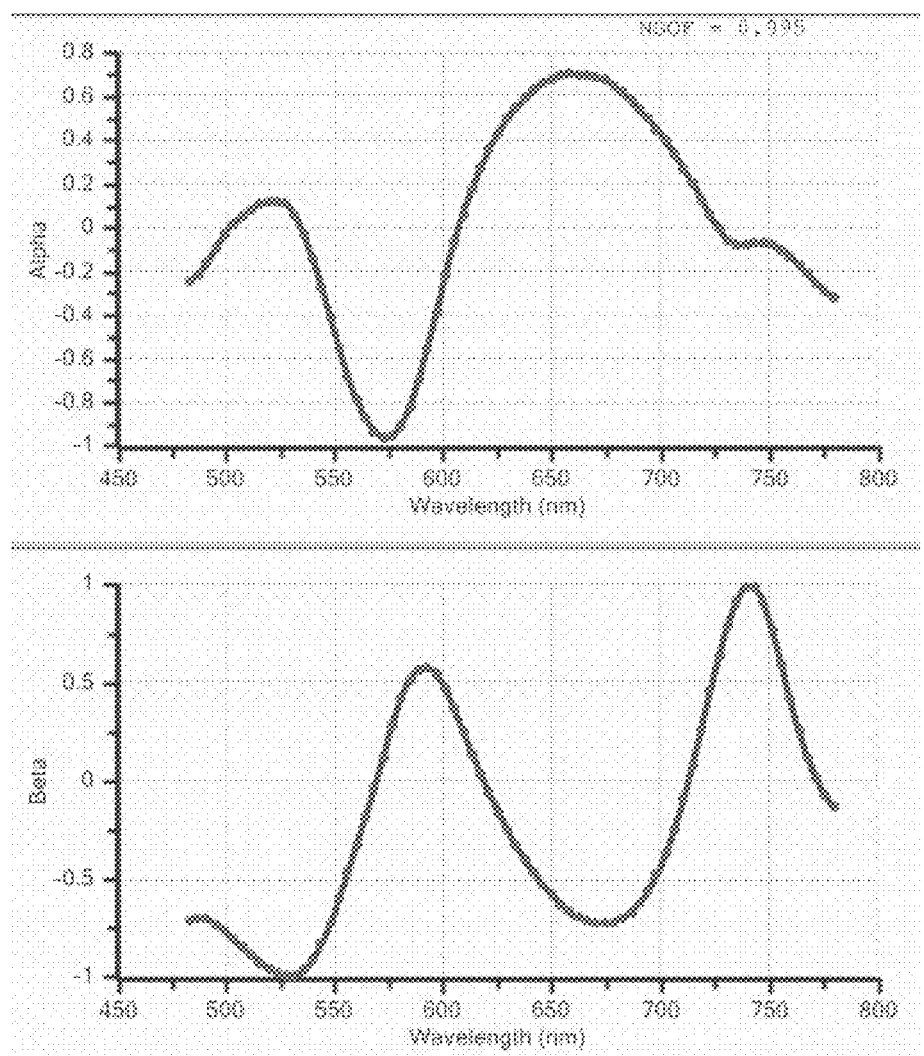

In terms of GOF, FIG. 3C shows that P1 has the highest rank. Therefore, we include the parameter in the further analysis. During this analysis, all the pre-defined floating parameters are floated as well as this parameter in the regression using the abnormal spectra. As shown in FIG. 3D, there is now a better GOF. It should be noted that if only the predefined floating parameters are floated, misleading information may result as if other parameter might compensate for the spectra difference.

FIGS. 4A-4E illustrate screenshots of a user interface of a software program executable to determine a parameter causing an abnormal semiconductor metrology measurement, in accordance with an embodiment. As an option, the screenshots may be implemented in the context of the method 100 of FIG. 1. Again, it should be noted that the aforementioned definitions may apply during the present description.

Figure 4A:
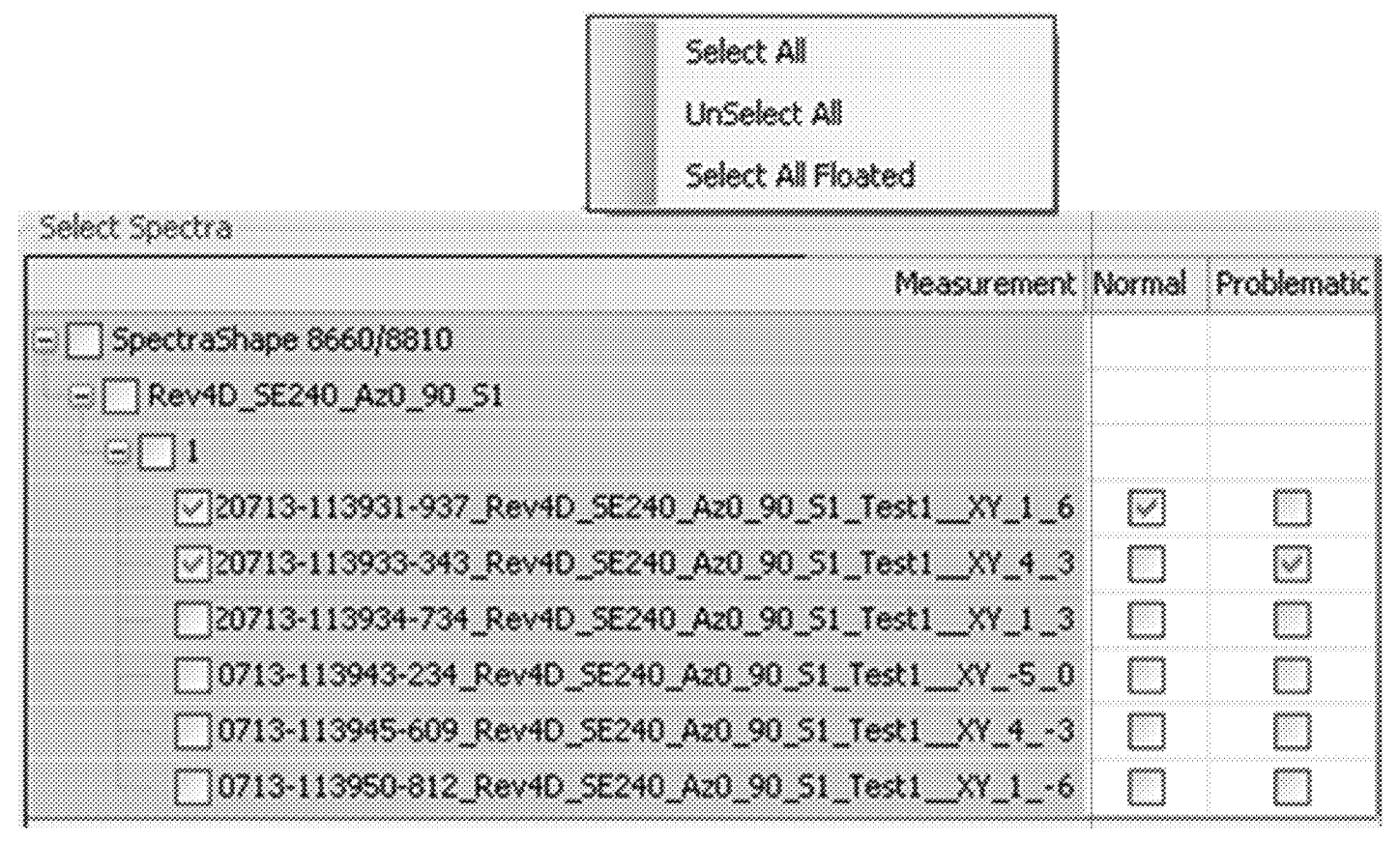

Initially, a user interacts with the software program executing on a computer. The software program receives an abnormal semiconductor metrology measurement and can then be used by the user to automatically identify which parameter caused the abnormal semiconductor metrology measurement. The user is provided with a measurement selection to select a normal spectra, as well as a measurement selection to select a problematic (or abnormal) spectra. This is shown in FIG. 4A. As also shown in FIG. 4A, a Context Menu is displayed when the user mouse right click on the Input table.

The user is provided with a parameter table shown in FIG. 4B, where all basis parameters are listed from the semiconductor model associated with the fabricated semiconductor component for which the abnormal measurement was received. The user defines the number of the top ranked parameters to be used during regression. The default number may be 5 and the valid number is between 0 and the total number of selected parameters.

The user selects either "Basic" or "Advanced" calculation option. There are the following columns in the parameter table: Select column (listing all and only model basis parameters, where the user can select any parameter on the select column regardless of floating or not in the model), Parameter name (read only), Nominal (normal) value (read only), Floated (read only where value comes from the model), Layer (i.e. building block name that is read only where single click on the column header [Select, Name, Float, or Layer] will sort the whole parameter table by this column), Analysis option radio buttons, "Top x ChiSq" or "ChiSq Improvement" If "ChiSq Improvement" is selected.

The software program includes a Run Button, and once clicked by the user, it will be disabled for double running of the same job and will be re-enabled again after a job is finished/canceled/failed. Once selected all input values are validated then the job is run based on the user's option of running locally or on a remote server. A Cancel button is also included, which is enabled once a job starts successfully and is disabled again once the job is finished or failed or canceled.

Table 1 illustrates examples of the validations that may be performed on user input values.

Table 1

At least one parameter is selected
The number of top rank parameter is [1, total parameters selected]
Exactly one normal spectra selected.
Exactly one problematic spectra selected.

Table 2 illustrates the regression operations that the computer may perform when running the job.

Table 2

A. Step one: Using project nominal profile with selected normal measurement. This is the baseline result.
B. Step two: Nominal profile applying baseline results using selected abnormal spectra
C. Step three: Loop through profiles where float only one of selected parameters at a time using the selected abnormal spectra with seeded profile from baseline resulted profile.
D. Step four: run basic or advance cases:
  1. Basic case: Nominal profile add one additional selected fixed parameter. If no fixed parameter fall into top rank then no results for step four.
  2. Advanced case: Nominal profile add two additional selected fixed parameters. If no fixed pair of parameters fall into top rank then no results for step four.

Figure 4C:
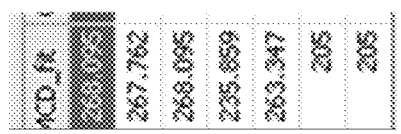
Figure 4D:
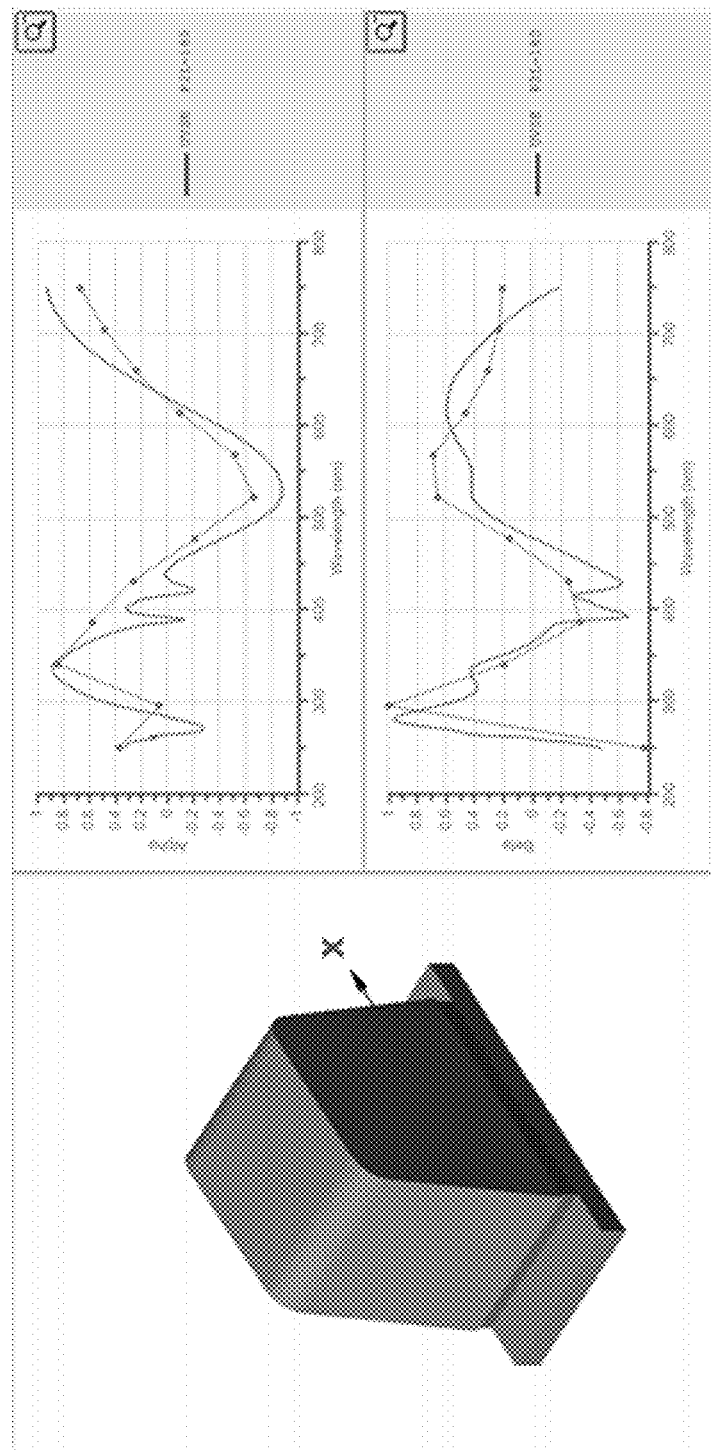
Figure 4E:
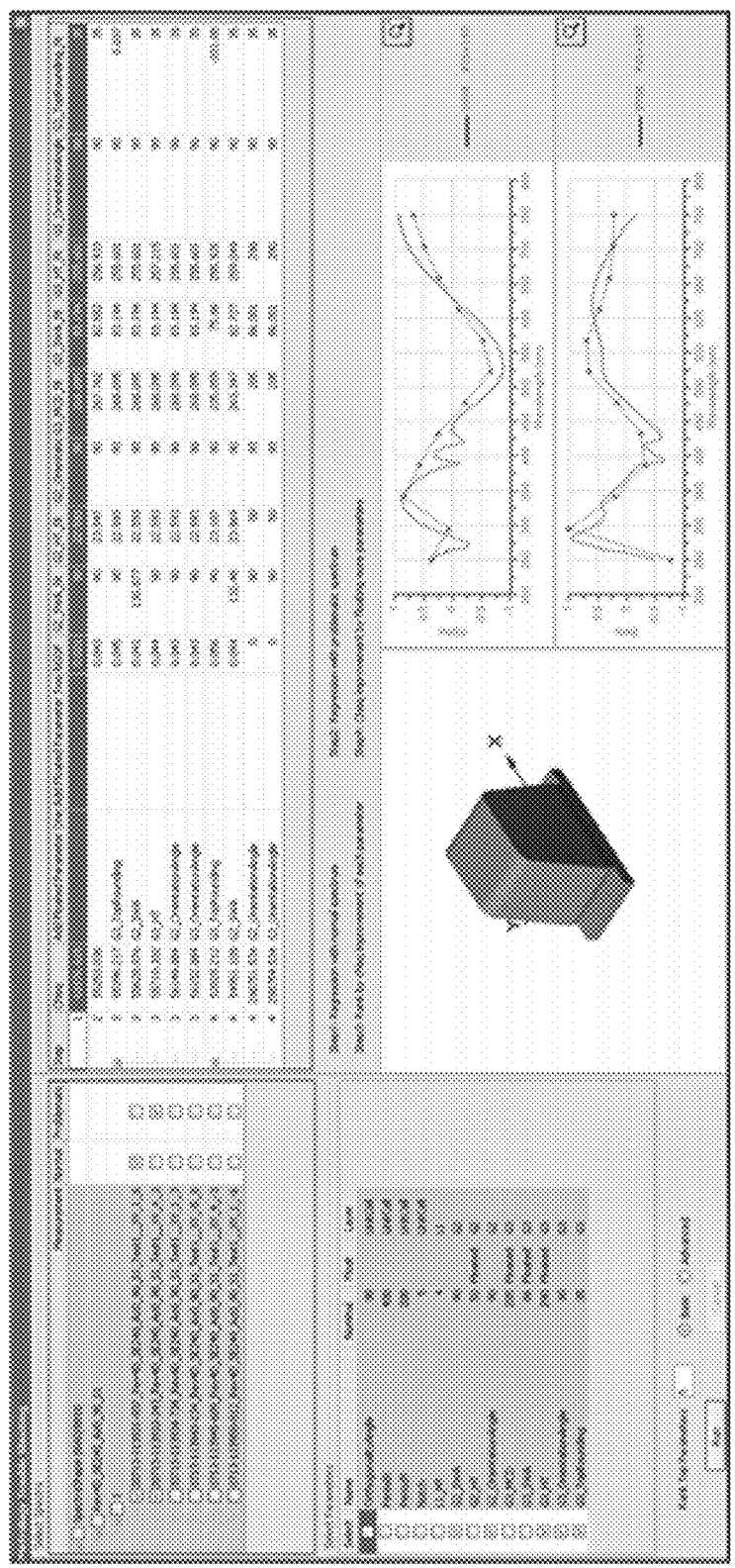

A results interface shown in FIG. 4C includes Row 1: Chisq for nominal Profile with normal spectra, Row 2: Chisq for nominal Profile with abnormal spectra, and Regression results including originally floated plus selected fixed parameters which are displayed after NGOF column. When the user selects a row, the corresponding profile and measurement and simulated spectra (see FIG. 4D) are displayed below the results table, as shown in FIG. 4E.

Figure 5:
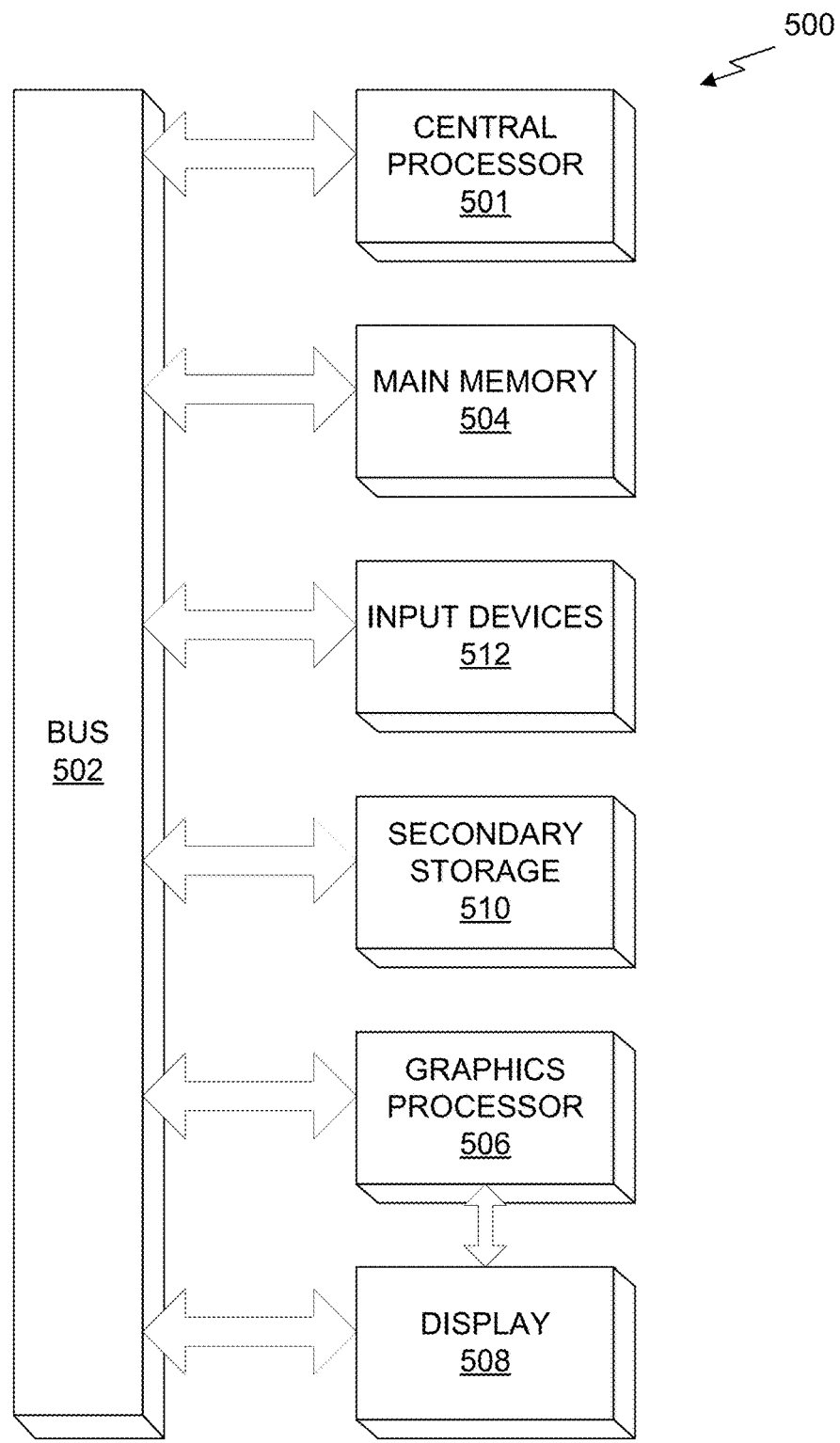
FIG. 5 illustrates an exemplary system in which the various architecture and/or functionality of the various previous embodiments may be implemented.

FIG. 5 illustrates an exemplary system 500 in which the various architecture and/or functionality of the various previous embodiments may be implemented. As shown, a system 500 is provided including at least one host processor 501 which is connected to a communication bus 502. The system 500 also includes a main memory 504. Control logic (software) and data are stored in the main memory 504 which may take the form of random access memory (RAM).

The system 500 also includes a graphics processor 506, input devices 512, and a display 508, i.e. a computer monitor. In one embodiment, the graphics processor 506 may include a plurality of shader modules, a rasterization module, etc. Each of the foregoing modules may even be situated on a single semiconductor platform to form a graphics processing unit (GPU).

In the present description, a single semiconductor platform may refer to a sole unitary semiconductor-based integrated circuit or chip. It should be noted that the term single semiconductor platform may also refer to multi-chip modules with increased connectivity which simulate on-chip operation, and make substantial improvements over utilizing a conventional central processing unit (CPU) and bus implementation. Of course, the various modules may also be situated separately or in various combinations of semiconductor platforms per the desires of the user.

The system 500 may also include a secondary storage 510. The secondary storage 510 includes, for example, a hard disk drive and/or a removable storage drive, representing a floppy disk drive, a magnetic tape drive, a compact disk drive, etc. The removable storage drive reads from and/or writes to a removable storage unit in a well known manner.

Computer programs, or computer control logic algorithms, may be stored in the main memory 504 and/or the secondary storage 510. Such computer programs, when executed, enable the system 500 to perform various functions. Memory 504, storage 510, volatile or non-volatile storage, and/or any other type of storage are possible examples of non-transitory computer-readable media.

In one embodiment, the architecture and/or functionality of the various previous figures may be implemented in the context of the host processor 501, graphics processor 506, an integrated circuit (not shown) that is capable of at least a portion of the capabilities of both the host processor 501 and the graphics processor 506, a chipset (i.e. a group of integrated circuits designed to work and sold as a unit for performing related functions, etc.), and/or any other integrated circuit for that matter.

Still yet, the architecture and/or functionality of the various previous figures may be implemented in the context of a general computer system, a circuit board system, a game console system dedicated for entertainment purposes, an application-specific system, and/or any other desired system. For example, the system 500 may take the form of a desktop computer, lap-top computer, and/or any other type of logic. Still yet, the system 500 may take the form of various other devices m including, but not limited to a personal digital assistant (PDA) device, a mobile phone device, a television, etc.

Further, while not shown, the system 500 may be coupled to a network [e.g. a telecommunications network, local area network (LAN), wireless network, wide area network (WAN) such as the Internet, peer-to-peer network, cable network, etc.) for communication purposes.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method, comprising:
   generating, by a metrology tool, an abnormal semiconductor metrology measurement from a semiconductor component fabricated by a semiconductor fabrication process by:
   outputting light, by a light system of the metrology tool, to illuminate the fabricated semiconductor component,
   capturing, by a collection system of the metrology tool, information describing an interaction of the light with the fabricated semiconductor component,
   analyzing, by a processing system of the metrology tool, the information to obtain measurements for the fabricated semiconductor component,
   determining, by the metrology tool, one of the measurements as abnormal with regards to a predefined model of the fabricated semiconductor component;
   receiving, by a computer processor from the metrology tool, the abnormal semiconductor metrology measurement;
   receiving, by the computer processor, an indication of a subset of parameters defined in the predefined model of the fabricated semiconductor component that are each potentially a cause of the abnormal semiconductor metrology measurement;
   for each of the parameters in the determined subset of parameters:
   adjusting, by the computer processor, a value of the parameter to be outside of a predefined value specified for the parameter in the model of the fabricated semiconductor component,
   determining, by the computer processor, a normal spectra response resulting from the adjusted parameter,
   comparing, by the computer processor, the normal spectra response to an abnormal spectra associated with the abnormal semiconductor metrology measurement to identify a spectra response difference therebetween;
   ranking, by the computer processor, the parameters in the determined subset of parameters, from least to most spectra response difference;
   in accordance with the ranking, selecting, by the computer processor, an N number of the ranked parameters in sequence beginning with the parameter corresponding to the least spectra response difference, where N is predefined and is less than a number of all the parameters defined in the model, and
   automatically determining, by the computer processor, the cause of the abnormal semiconductor metrology measurement, from the one or more of the selected parameters by:
   performing, by the computer processor, regression in association with each of the selected parameters and automatically identifying from the regression one or more of the selected parameters as the at least one parameter of the fabricated semiconductor component causing the abnormal semiconductor metrology measurement; and
   providing the determined cause of the abnormal semiconductor metrology measurement for use in facilitating process controls in the semiconductor fabrication process.

2. The method of claim 1, wherein the subset of parameters of the fabricated semiconductor component determined to be potential causes of the abnormal semiconductor metrology measurement includes at least one parameter defined as a floating parameter in the model of the fabricated semiconductor component.

3. The method of claim 2, wherein the at least one parameter is defined as a floating parameter by defining a range of values for the at least one parameter.

4. The method of claim 1, wherein the subset of parameters of the fabricated semiconductor component determined to be potential causes of the abnormal semiconductor metrology measurement includes at least one parameter defined as a fixed parameter in the model of the fabricated semiconductor component.

5. The method of claim 4, wherein the at least one parameter is defined as a fixed parameter by defining a fixed value for the at least one parameter.

6. The method of claim 1, wherein the subset of parameters of the fabricated semiconductor component determined to be potential causes of the abnormal semiconductor metrology measurement include at least one first parameter defined as a floating parameter in the model of the fabricated semiconductor component and at least one second parameter defined as a fixed parameter in the model of the fabricated semiconductor component.

7. The method of claim 1, wherein the subset of parameters of the fabricated semiconductor component that are determined as potential causes of the abnormal semiconductor metrology measurement include parameters in the model of the fabricated semiconductor component that have been selected by a user.

8. The method of claim 1, wherein the ranking is in order of a goodness of fit for the spectra response difference.

9. The method of claim 1, wherein the parameters in the determined subset of parameters are ranked in order from closest correlation to farthest correlation.

10. The method of claim 1, wherein N is predetermined by a user.

11. The method of claim 1, wherein N is between 0 and a number of parameters in the subset of parameters of the fabricated semiconductor component that are determined as potential causes of the abnormal semiconductor metrology measurement.

12. The method of claim 1, wherein performing regression in association with each of the selected parameters and automatically identifying from the regression the one or more of the selected parameters as the at least one parameter of the fabricated semiconductor component causing the abnormal semiconductor metrology measurement includes:
    performing a first regression with a normal spectra,
    recording results of the first regression, including values for the parameters in the model of the fabricated semiconductor component, as a baseline,
    for each individual one of the selected parameters or a combination of two or more of the selected parameters, performing a second regression with an abnormal spectra associated with the abnormal measurement using an adjusted value of the individual selected parameter or the combined two or more of the selected parameters and using values for remaining parameters of the fabricated semiconductor component fixed at the baseline,
    recording results of the second regression, and
    determining a deviation between each of the results of the first regression and the corresponding result of the second regression,
    identifying the individual one of the selected parameters or the combined two or more of the selected parameters having the least deviation as the at least one parameter of the fabricated semiconductor component causing the abnormal semiconductor metrology measurement.

13. The method of claim 12, further comprising displaying a result of the regression that includes a list of the selected parameters based on each parameter's deviation from the corresponding baseline value.

14. The method of claim 13, wherein the result of the regression further includes, for each of selected parameters, the deviation from the corresponding baseline value.

15. An apparatus, comprising:
    a metrology tool that generates an abnormal semiconductor metrology measurement from a semiconductor component fabricated by a semiconductor fabrication process, the metrology tool including:
        a light system that outputs light to illuminate the fabricated semiconductor component,
        a collection system that captures information describing an interaction of the light with the fabricated semiconductor component,
        a processing system that analyzes the information to obtain measurements for the fabricated semiconductor component and that determines one of the measurements as abnormal with regards to a predefined model of the fabricated semiconductor component;
    one or more hardware processors for:
        receiving, from the metrology tool, the abnormal semiconductor metrology measurement;
        receiving an indication of a subset of parameters defined in the predefined model of the fabricated semiconductor component that are each potentially a cause of the abnormal semiconductor metrology measurement;
        for each of the parameters in the determined subset of parameters:
            adjusting a value of the parameter to be outside of a predefined value specified for the parameter in the model of the fabricated semiconductor component,
            determining a normal spectra response resulting from the adjusted parameter,
            comparing the normal spectra response to an abnormal spectra associated with the abnormal semiconductor metrology measurement to identify a spectra response difference therebetween;
        ranking the parameters in the determined subset of parameters, from least to most spectra response difference;
        in accordance with the ranking, selecting an N number of the ranked parameters in sequence beginning with the parameter corresponding to the least spectra response difference, where N is predefined and is less than a number of all the parameters defined in the model; and
        automatically determining, by the computer processor, the cause of the abnormal semiconductor metrology measurement, from the one or more of the selected parameters by:
            performing regression in association with each of the selected parameters and automatically identifying from the regression one or more of the selected parameters as the at least one parameter of the fabricated semiconductor component causing the abnormal semiconductor metrology measurement; and
        providing the determined cause of the abnormal semiconductor metrology measurement for use in facilitating process controls in the semiconductor fabrication process.

16. The apparatus of claim 15, the apparatus further comprising memory for storing the model of the fabricated semiconductor component, wherein the subset of parameters of the fabricated semiconductor component determined to be potential causes of the abnormal semiconductor metrology measurement include at least one first parameter defined as a floating parameter in the model of the fabricated semiconductor component and at least one second parameter defined as a fixed parameter in the model of the fabricated semiconductor component.

17. The apparatus of claim 15, wherein performing regression in association with each of the selected parameters and automatically identifying from the regression the one or more of the selected parameters as the at least one parameter of the fabricated semiconductor component causing the abnormal semiconductor metrology measurement includes:

performing a first regression with a normal spectra, recording results of the first regression, including values for the parameters in the model of the fabricated semiconductor component, as a baseline, for each individual one of the selected parameters or a combination of two or more of the selected parameters, performing a second regression with an abnormal spectra associated with the abnormal measurement using an adjusted value of the individual selected parameter or the combined two or more of the selected parameters and using values for remaining parameters of the fabricated semiconductor component fixed at the baseline, recording results of the second regression, and determining a deviation between each of the results of the first regression and the corresponding result of the second regression, identifying the individual one of the selected parameters or the combined two or more of the selected parameters having the least deviation as the at least one parameter of the fabricated semiconductor component causing the abnormal semiconductor metrology measurement.

* * * * *